United States Patent [19]
Mansfeld et al.

[11] Patent Number: 5,968,535
[45] Date of Patent: Oct. 19, 1999

[54] DENATURANT FOR ETHANOL

[75] Inventors: Gerd Mansfeld, Eschershausen; Egon Oelkers, Bevern; Klaus Peters, Holzminden, all of Germany

[73] Assignee: Haarmann & Reimer GmbH, Germany

[21] Appl. No.: 09/053,320

[22] Filed: Apr. 1, 1998

[30] Foreign Application Priority Data

Apr. 9, 1997 [DE] Germany .......................... 197 14 580

[51] Int. Cl.⁶ ................... A61K 7/00; A61K 7/32; C09K 3/00; C12F 5/00
[52] U.S. Cl. .......................... 424/401; 252/365; 252/366; 424/65; 424/70.1; 512/1
[58] Field of Search ..................... 252/365, 366; 424/401, 65, 70.1; 512/1

[56] References Cited

U.S. PATENT DOCUMENTS

| | | | |
|---|---|---|---|
| 4,319,886 | 3/1982 | Gold et al. | 44/53 |
| 4,438,046 | 3/1984 | Grew et al. | 562/493 |
| 5,747,021 | 5/1998 | McKenzie et al. | 424/73 |
| 5,843,881 | 12/1998 | Dubois et al. | 512/1 |

FOREIGN PATENT DOCUMENTS

| | | |
|---|---|---|
| 66638 | 3/1973 | Poland . |
| 486038 | 11/1980 | Spain . |

*Primary Examiner*—Jose' G. Dees
*Assistant Examiner*—Marina Lamm
*Attorney, Agent, or Firm*—Brinks Hofer Gilson & Lione

[57] ABSTRACT

The invention relates to a denaturant for ethanol, to ethanol comprising this denaturant and to cosmetic products comprising this denatured ethanol.

11 Claims, No Drawings

DENATURANT FOR ETHANOL

BACKGROUND OF THE INVENTION

1. Field of the Invention

The invention relates to a denaturant for ethanol, to ethanol comprising this denaturant and to cosmetic products comprising this denatured ethanol.

2. Discussion of the Background

Ethyl alcohol which is not intended for foods and confectionery, such as, for example, ethyl alcohol for the preparation of cosmetics, has for tax reasons to be rendered unusable for ingestion by the addition of denaturants. Different denaturants are used for this purpose within Europe and outside Europe. The denaturant which is used most frequently throughout the world is diethyl phthalate. In many countries, natural ethereal oils and various individual components, such as, for example, isopropanol, phenylethyl alcohol, musk ketone etc., are also used for denaturing.

All known denaturants have disadvantages (some of them considerable) which lower the product quality. Diethyl phthalate, for example, in aerosol formulations causes sneezing and, as is the case for all one-component additives, has an uncontrollable influence on scent development of perfumed additives. Other denaturants, such as, for example, isopropanol and musk ketone, influence the odour character of perfumed products and some of them (musk ketone) are known to be colour-unstable.

SUMMARY OF THE INVENTION

The object of the invention was to develop a denaturant which has a denaturing effect similar to that of diethyl phthalate, but does not have the disadvantages described; in particular, the novel denaturant was to have a weak intrinsic odour which harmonizes with all perfume compositions. A composition has been found which meets the described requirements.

DESCRIPTION OF THE INVENTION

The invention thus provides a composition comprising

A. 50–250, preferably
  80–120 parts by weight of benzyl salicylate,
B. 5–40 parts by weight of (i) 4.6.6.7.8.8.-hexamethyl-1.3.4.6.7.8.-hexahydrocyclopenta[g]benzopyran or (ii) oxacyclo-hexadec-12- and/or -13-en-2-one, each of which may be dissolved in 5 to 40 parts by weight of (E and/or F),
C. 10–100, preferably
  30–70 parts by weight of $C_1$–$C_4$-alkyl esters of hydrogenated root oil, preferably the methyl ester,
D. 40–240, preferably
  75–125 parts by weight of 2-pentylphenylpropanol,
E. 200–500,
  preferably 250–350 parts by weight of benzyl benzoate,
F. 100–400,
  preferably 150–250 parts by weight of dipropylene glycol and
G. 150–300,
  preferably 150–250 parts by weight of triethyl citrate.

Compound B (i) conforms to the formula

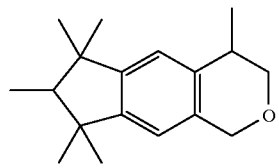

and is sold by Bush Boake Allen/Great Britain under the name ABBALIDE® and by International Flavors & Fragrances/USA under the name Galaxolide®.

Component B (ii) is sold as an isomeric mixture by Bayer AG under the name GLOBALID®.

Component C is sold by Hercules/USA under the name HERCOLYN D-E®.

The compositions according to the invention can be prepared by mixing the individual components. For denaturing ethanol, suitable concentrations of the compositions according to the invention are in the range from 0.01 to 5 kg, preferably from 0.01 to 3 kg per 100 l of ethanol. The invention further provides ethanol comprising the described compositions.

The invention further provides cosmetic products prepared using the ethanol denatured according to the invention. These products may comprise from 1 to 99% by weight, based on ethanol-containing cosmetic product, of the denatured ethanol.

Such cosmetic products include (preferred ethanol content in brackets) extract, eau de parfum, eau de toilette, eau de Cologne (in each case 30–99% by wt.), splash Cologne, aftershave, general deodorant formulations, hair setting lotions, hairspray, hair gels (1–50% by wt.), face lotion (5–70% by wt.), body gels, in particular emulsions (in each case 1–40% by wt.), hair tonic (10–75% by wt.), hand disinfectants (20–99% by wt.), glass cleaners (10–90% by wt.), freshening wipes (30–90% by wt.) etc.

The parts and percentage data of the following examples refer in each case to the weight.

EXAMPLES

Example 1

| Parts | Substance |
| --- | --- |
| 100.00 | Benzyl salicylate |
| 50.00 | Chromanolid, 50% in benzyl benzoate |
| 50.00 | Hercolyn D-E |
| 100.00 | 2-Pentylphenylpropanol |
| 300.00 | Benzyl benzoate |
| 200.00 | Dipropylene glycol |
| 200.00 | Triethyl citrate |

700 g of the above composition are mixed with 100 l of ethanol. The resulting denatured ethanol is outstandingly suitable for preparing cosmetic products.

Example 2

| Parts | Substance |
| --- | --- |
| 100.00 | Benzyl salicylate |
| 50.00 | Globalid, 50% in dipropylene glycol |
| 50.00 | Herolyn D-E |

-continued

| Parts | Substance |
|---|---|
| 100.00 | 2-Pentylphenylpropanol |
| 300.00 | Benzyl benzoate |
| 200.00 | Dipropylene glycol |
| 200.00 | Triethyl citrate |

700 g of the above composition are mixed with 100 l of ethanol. The resulting denatured ethanol is outstandingly suitable for preparing cosmetic products.

We claim:

1. A composition comprising:
   (A) 50–250 parts by weight of benzyl salicylate,
   (B) 5–40 parts by weight of (I) 4.6.6.7.8.8.-hexamethyl-1.3.4.6.7.8.-hexahydrocyclopenta[g]benzopyran or (ii) oxacyclo-hexadec-12- and/or -13-en-2-one, each of which may be dissolved in 5 to 50 parts by weight of (E and/or F),
   (C) 10–100 parts by weight of $C_1$–$C_4$-alkyl esters of hydrogenated root oil,
   (D) 40–240 parts by weight of 2-pentylphenylpropanol,
   (E) 200–500 parts by weight of benzyl benzoate,
   (F) 100–400 parts by weight of dipropylene glycol, and
   (G) 150–300 parts by weight of triethyl citrate.

2. The composition of claim 1, comprising 80–120 parts by weight of (A).

3. The composition of claim 1, comprising 30–70 parts by weight of (C).

4. The composition of claim 1, comprising 75–125 parts by weight of (D).

5. The composition of claim 1, comprising 250–350 parts by weight of (E).

6. The composition of claim 1, comprising 150–250 parts by weight of (F).

7. The composition of claim 1, comprising 150–250 parts by weight of (G).

8. Ethanol comprising 0.01 to 5 kg of a denaturant composition per 100 L of ethanol, wherein said denaturant composition comprising:
   (A) 50–250 parts by weight of benzyl salicylate,
   (B) 5–40 parts by weight of (I) 4.6.6.7.8.8.-hexamethyl-1.3.4.6.7.8.-hexahydrocyclopenta[g]benzopyran or (ii) oxacyclo-hexadec-12- and/or -13-en-2-one, each of which may be dissolved in 5 to 50 parts by weight of (E and/or F),
   (C) 10–100 parts by weight of $C_1$–$C_4$-alkyl esters of hydrogenated root oil,
   (D) 40–240 parts by weight of 2-pentylphenylpropanol,
   (E) 200–500 parts by weight of benzyl benzoate,
   (F) 100–400 parts by weight of dipropylene glycol and
   (G) 150–300 parts by weight of triethyl citrate.

9. The ethanol of claim 8, comprising 0.01 to 3 kg of the denaturant composition per 100 L of ethanol.

10. A cosmetic product comprising ethanol comprising:
    (A) 50–250 parts by weight of benzyl salicylate,
    (B) 5–40 parts by weight of (I) 4.6.6.7.8.8.-hexamethyl-1.3.4.6.7.8.-hexahydrocyclopenta[g]benzopyran or (ii) oxacyclo-hexadec-12- and/or -13-en-2-one, each of which may be dissolved in 5 to 50 parts by weight of (E and/or F),
    (C) 10–100 parts by weight of $C_1$–$C_4$-alkyl esters of hydrogenated root oil,
    (D) 40–240 parts by weight of 2-pentylphenylpropanol,
    (E) 200–500 parts by weight of benzyl benzoate,
    (F) 100–400 parts by weight of dipropylene glycol and
    (G) 150–300 parts by weight of triethyl citrate.

11. The cosmetic product of claim 10, comprising 0.01 to 3 kg of the denaturant composition per 100 L of ethanol.

* * * * *